United States Patent
Dib

(10) Patent No.: US 6,642,262 B2
(45) Date of Patent: Nov. 4, 2003

(54) RILUZOLE AND ALPHA-TOCOPHEROL COMBINATION

(75) Inventor: Michel Dib, Paris (FR)

(73) Assignee: Aventia Pharma S.A., Antony Cedex (FR)

( * ) Notice: Subject to any disclaimer, the term of this patent is extended or adjusted under 35 U.S.C. 154(b) by 153 days.

(21) Appl. No.: 09/854,318

(22) Filed: May 11, 2001

(65) Prior Publication Data

US 2002/0019426 A1 Feb. 14, 2002

Related U.S. Application Data

(63) Continuation of application No. PCT/FR99/02753, filed on Nov. 9, 1999.

(30) Foreign Application Priority Data

Nov. 13, 1998 (FR) .............................. 98 14250

(51) Int. Cl.⁷ ............................. A61K 31/355
(52) U.S. Cl. ...................... 514/367; 514/428
(58) Field of Search ................. 514/367, 458

(56) References Cited

U.S. PATENT DOCUMENTS 5,780,489 A * 7/1998 Brooks ........................ 514/369
5,849,290 A * 12/1998 Brown et al. ............... 424/94.4
5,964,224 A * 10/1999 Kaji ............................ 128/897

OTHER PUBLICATIONS

Ross, M.A.: "Acquired motor neuron disorders" *Neurologic Clinics* (*Neurol. Clin.*), 1997, 15/3 pp. (481–500).
Gurney, ME., et al: "Pathogenic mechanisms in familial amyotrophic lateral sclerosis due to mutation of Cu, Zn superoxide dismutase" *Pathol Biol* (Paris), Jan. 1996, 44(1) pp. 51–56.
Miller, R.G.: "New approaches to therapy of amyotrophic lateral sclerosis" *Western Journal of Medicine* (*West.J.Med*), 168/4 pp. 262–263 (1998).
Riviere, M., et al: *Arch Neurol.*, 55, pp. 526–528 (1998).
Lacomblez, L., et al: *The Lancet*, 347, pp. 1425–1431 (1996).
Bensimon, A.E.: *The New England Journal of Medicine*, 330, pp. 585–591 (1994).
Favier et al: *Analysis of Free Radicals in Biological Systems*, Birk Hauser, Basel/Switzerland (1995) pp. 100–117.

* cited by examiner

*Primary Examiner*—James H. Reamer
(74) *Attorney, Agent, or Firm*—Balaram Gupta

(57) ABSTRACT

The invention concerns a combination of alpha-tocopherol and riluzole or a pharmaceutically acceptable salt thereof and the use of said combination for treating amyotrophic lateral sclerosis.

16 Claims, No Drawings

RILUZOLE AND ALPHA-TOCOPHEROL COMBINATION

This application is a continuation of International application No. PCT/FR99/02,753, filed Nov. 09, 1999; which claims the benefit of priority of French Patent Application No. 98/14,250, filed Nov. 13, 1998.

The present invention relates to the combination of α-tocopherol and of riluzole or of a pharmaceutically acceptable salt of this compound and the use of this combination for the treatment of amyotrophic lateral sclerosis (ALS).

Amyotrophic lateral sclerosis, also known by the name of CHARCOT's disease and LOU GEHRIG's disease, was described for the first time by CHARCOT in 1865. ALS is a fatal disease resulting from degeneration of the motoneurons. The disease is accompanied by progressive paralysis, leading to the loss of motor and respiratory functions and then to death within a period of two to eight years after the appearance of the first symptoms.

To date, only riluzole (2-amino-6-trifluoromethoxybenzothiazole) is marketed under the name RILUTEK® for the treatment of amyotrophic lateral sclerosis. Riluzole makes it possible mainly to slow down the progression of the disease.

It has now been found that the combination of riluzole or one of its pharmaceutically acceptable salts and of α-tocopherol (vitamin E) makes it possible to slow down the disease more substantially than riluzole alone and also to reduce fatigue in patients and the plasma concentration of malondialdehyde.

The study was carried out in 289 patients in total aged over 18 years, who have been suffering from ALS for less than 5 years and in whom the vital capacity/theoretical normal vital capacity ratio is greater than or equal to 60% (the vital capacity is a routine conventional measurement of the respiratory function also called lung function test).

The patients are divided into 2 groups:
group 1: 145 patients treated with 100 mg/day of riluzole by the oral route and 1000 mg/day of α-tocopherol by the oral route,
group 2: 144 patients treated with 100 mg/day of riluzole by the oral route and placebo.

Some patients in the 2 groups no longer meeting, in a second evaluation, the inclusion criteria or who had not followed the treatment correctly, were not taken into account for the determination of the results.

The patients are monitored for a year. The results are measured on functional scales (Munsat's functional states (RIVIERE et al., Arch. Neurol., 55, 526 (1998)), a visual analog scale (VAS) for fatigability (LACOBLEZ et al., The Lancet, 347, 1425 (1996); BENSIMON et al., New England Journal of Medicine, 330, 585 (1994)) and plasma concentration of malondialdehyde, a biochemical marker for oxidative stress (FAVIER, Analysis of free radicals in biological systems, Birk Hauser, Basel/Switzerland, 1995 p. 100–117).

The Munsat functional state A relates to patients in an average or mild state:
average state: average deficiency in 3 regions (speech, arm and leg), functionally independent in speech, activities of the upper extremities in daily and ambulatory life,
mild state: average deficiency in 3 regions or mild to severe deficiency in one region while the other two regions are normal or slightly affected.

The Munsat functional state B relates to patients in the severe or final state:
severe state: need for assistance in 2 or 3 regions, dysarthric speech and/or patients requiring assistance to walk and/or requiring assistance for the activities of the upper extremities in daily life,
final state: nonfunctional use of at least 2 regions and mild or nonfunctional use of the third region.

The progression of the functional states A and B is determined at the time of inclusion (M0) and after 12 months of treatment (M12). The results obtained are the following:

|  | RILUZOLE AND PLACEBO (number of patients) | RILUZOLE AND α-TOCOPHEROL (number of patients) |
|---|---|---|
| Condition on inclusion (M0) |  |  |
| state A | 109 | 112 |
| state B | 10 | 10 |
| Condition after treatment (M12) |  |  |
| state A | 56 | 73 |
| state B | 63 | 49 |

These results demonstrate that, after 12 months of treatment with riluzole and placebo, 53 patients (44.5%) exhibited a worsening of the disease and 66 patients (55.3%) did not exhibit any change, whereas in the patients treated with the riluzole and α-tocopherol combination, only 39 patients (32%) exhibited a worsening and 83 patients (68%) did not exhibit any change.

The progression of the disease is therefore more reduced with the riluzole and α-tocopherol combination than with riluzole alone.

Fatigability is measured according to the visual analog scale (VAS) on inclusion of the patients (M0) and at 3 months (M3).

In this test, the mean values obtained are the following:

|  | VAS at M0 (mm) | VAS at M3 (mm) | Δ M0-M3 (mm) |
|---|---|---|---|
| RILUZOLE AND PLACEBO (115 patients) | 48.4 | 65.7 | 17.3 |
| RILUZOLE AND α-TOCOPHEROL COMBINATION (118 patients) | 46.4 | 58.6 | 12.2 |

These values clearly demonstrate that the patients treated with the riluzole and α-tocopherol combination are less tired than the patients treated with riluzole and placebo.

The plasma concentration of malondialdehyde, which is thought to be a predictive factor for the progression of ALS, was determined at the time of inclusion of the patients (M0) and at 3 months (M3).

The mean values of the concentrations obtained are the following:

|  | Concentration at M0 ($\mu$M) | Concentration at M3 ($\mu$M) | Δ M3-M0 ($\mu$M) |
|---|---|---|---|
| RILUZOLE AND PLACEBO (65 patients) | 2.94 ± 0.40 | 2.72 ± 0.40 | 0.22 ± 0.40 |
| RILUZOLE AND α-TOCOPHEROL COMBINATION (58 patients) | 2.86 ± 0.40 | 2.36 ± 0.30 | 0.50 ± 0.50 |

These results demonstrate that the plasma concentration of malondialdehyde is increased in patients suffering from amyotrophic lateral sclerosis (concentrations at M0) and decreases during the treatment but more significantly with the riluzole and α-tocopherol combination than with riluzole alone.

As pharmaceutically acceptable salts of riluzole, there may be mentioned in particular the addition salts with inorganic acids such as hydrochloride, sulphate, nitrate and phosphate, or organic acids such as acetate, propionate, succinate, oxalate, benzoate, fumarate, maleate, methanesulfonate, isethionate, theophilline acetate, salicylate, phenolphthalinate, methylene-bis-β-oxynaphthoate or substitution derivatives of these derivatives.

The combination may be used by the oral, parenteral or rectal route, either simultaneously or separately or spaced out over time.

The present invention also relates to the pharmaceutical compositions comprising the combination of riluzole and of α-tocopherol in the pure state or in the form of a combination with one or more compatible and pharmaceutically acceptable diluents and/or adjuvants and/or optionally in combination with another pharmaceutically compatible and physiologically active product.

As solid compositions for oral administration, use may be made of tablets, pills, powders (gelatin capsules, cachets) or granules. In these compositions, the active ingredients are mixed with one or more inert diluents, such as starch, cellulose, sucrose, lactose or silica, under an argon stream. These compositions may also comprise substances other than the diluents, for example one or more lubricants such as magnesium stearate or talc, a coloring, a coating (sugar-coated tablets) or a glaze.

As liquid compositions for oral administration, use may be made of pharmaceutically acceptable solutions, suspensions, emulsions, syrups and elixirs containing inert diluents such as water, ethanol, glycerol, vegetable oils or paraffin oil. These compositions may comprise substances other than the diluents, for example wetting products, sweeteners, thickeners, flavorings or stabilizers.

The sterile compositions for parenteral administration may be preferably solutions which are aqueous or nonaqueous, suspensions or emulsions. As solvent or vehicle, use may be made of water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be performed in several ways, for example by asepticizing filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active ingredient, excipients such as cocoa butter, semisynthetic glycerides or polyethylene glycols.

The present invention also relates to the method of treating patients suffering from amyotrophic lateral sclerosis, which consists in administering to the patient a combination of α-tocopherol and of riluzole or of one of its pharmaceutically acceptable salts either simultaneously or separately or spaced out over time.

The doses depend on the desired effect, the duration of the treatment and the route of administration used; they are generally from 10 to 400 mg per day by the oral route for an adult with unit doses ranging from 10 to 200 mg of riluzole and from 250 to 4000 mg per day by the oral route for an adult with unit doses of 100 to 1000 mg of α-tocopherol.

In general, the doctor will determine the appropriate dosage according to the age, weight and all the other factors specific to the subject to be treated.

What is claimed is:

1. A pharmaceutical composition comprising a combination of α-tocopherol and riluzole or of a pharmaceutically acceptable salt thereof.

2. The composition according to claim 1 wherein 10 to 400 parts by weight of riluzole are used per 250 to 4000 parts by weight of α-tocopherol.

3. The composition according to claim 1 wherein the combination is used simultaneously, separately or spaced out over time.

4. The composition according to claim 1 wherein the combination is used simultaneously.

5. The composition according to claim 2 wherein the combination is used simultaneously, separately or spaced out over time.

6. The composition according to claim 2 wherein the combination is used simultaneously.

7. The composition according to claim 1 for the treatment of amyotrophic lateral sclerosis.

8. The composition according to claim 2 for the treatment of amyotrophic lateral sclerosis.

9. The composition according to claim 3 for the treatment of amyotrophic lateral sclerosis.

10. The composition according to claim 4 for the treatment of amyotrophic lateral sclerosis.

11. The composition according to claim 5 for the treatment of amyotrophic lateral sclerosis.

12. The composition according to claim 6 for the treatment of amyotrophic lateral sclerosis.

13. The composition according to claim 1 wherein the combination is in the pure state or in the presence of any compatible and pharmaceutically acceptable diluent or adjuvant.

14. A process for producing a pharmaceutical composition comprising combining α-tocopherol and riluzole or of a pharmaceutically acceptable salt thereof.

15. A process according to claim 14, wherein the pharmaceutical composition prepared is useful in the treatment of amyotrophic lateral sclerosis.

16. A process according to claim 15, wherein the pharmaceutical composition prepared is useful in inhibiting degeneration of the motoneurons.

* * * * *